(12) United States Patent
Muehleisen

(10) Patent No.: US 8,561,454 B2
(45) Date of Patent: Oct. 22, 2013

(54) PHOTOACOUSTIC SENSOR

(75) Inventor: Ralph Muehleisen, Oak Park, IL (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/202,356

(22) PCT Filed: Oct. 28, 2010

(86) PCT No.: PCT/US2010/054417
§ 371 (c)(1),
(2), (4) Date: Aug. 19, 2011

(87) PCT Pub. No.: WO2012/057760
PCT Pub. Date: May 3, 2012

(65) Prior Publication Data
US 2012/0103065 A1    May 3, 2012

(51) Int. Cl.
*G01N 21/00*    (2006.01)
*G01N 29/02*    (2006.01)

(52) U.S. Cl.
USPC ............................. 73/24.02; 356/432; 356/437

(58) Field of Classification Search
USPC .......... 73/24.02; 356/436, 437, 438, 440, 432
See application file for complete search history.

(56) References Cited

U.S. PATENT DOCUMENTS

| | | | |
|---|---|---|---|
| 4,622,845 A * | 11/1986 | Ryan et al. | ................ 73/24.02 |
| 4,740,086 A | 4/1988 | Oehler et al. | |
| 5,753,797 A | 5/1998 | Forster et al. | |
| 5,824,884 A * | 10/1998 | Olender et al. | ............ 73/40.5 A |
| 6,216,025 B1 | 4/2001 | Kruger | |
| 6,843,102 B1 * | 1/2005 | Shulga et al. | ................ 73/25.01 |
| 7,409,117 B2 * | 8/2008 | Von Drasek et al. | ............. 385/12 |
| 7,683,357 B2 * | 3/2010 | Von Drasek et al. | .......... 250/573 |
| 7,924,423 B2 * | 4/2011 | Van Neste et al. | ............ 356/432 |
| 2003/0089170 A1 | 5/2003 | Amonette et al. | |

(Continued)

FOREIGN PATENT DOCUMENTS

| CH | 679076 A5 | 12/1991 |
|---|---|---|
| DE | 4018393 A1 | 12/1990 |
| EP | 0151474 A2 | 8/1985 |
| GB | 2190998 A | 12/1987 |

OTHER PUBLICATIONS

"Optical Modulators", Encyclopedia of Laser Physics and Technology, Jul. 26, 2008, Accessed online at <http://www.rp-photonics.com/optical_modulators.html>.*

(Continued)

*Primary Examiner* — Lisa Caputo
*Assistant Examiner* — Punam Roy
(74) *Attorney, Agent, or Firm* — Ren-Sheng International

(57) ABSTRACT

A photoacoustic gas sensor, system and method is generally described. In some examples, a photoacoustic gas sensor includes a MEMS-based wavelength-selective optical modulator and a ring array of acoustic sensors. The MEMS-based optical modulator can be adapted to provide flexible wavelength selectivity such that a large number of chemical compounds may be detected. The ring array of acoustic sensors can be adapted to measure photoacoustically generated acoustic signals without the need for resonant enhancement of a photoacoustic cell of the gas sensor. In some examples, a unique uncorrelated and deterministic signal may be used to modulate each light wavelength of interest. Signal processing may be used that allows the simultaneous measurement of the absorption spectra of multiple optical wavelengths as well as the rejection of unwanted acoustic noise.

19 Claims, 5 Drawing Sheets

(56) References Cited

U.S. PATENT DOCUMENTS

| | | | |
|---|---|---|---|
| 2007/0151325 A1* | 7/2007 | Kauppinen | 73/24.02 |
| 2010/0027012 A1 | 2/2010 | Fritz et al. | |
| 2010/0242572 A1* | 9/2010 | Yu | 73/24.02 |

OTHER PUBLICATIONS

Andreas Mandelis, "Time-Delay-Domain and Pseudorandom-Noise Photoacoustic and Photothermal Wave Processes: A Review of the State of the Art," IEEE Transactions on Ultrasonics, Ferroelectrics and Frequency Control, Sep. 1986, pp. 590-614, vol. UFFC-33.

Yoshinori Sugitanj and Akinori Uejima, "Effect of M-series PRBS Modulation on the Time Resolution in Correlation Photoacoustics," Bulletin of the Chemical Society of Japan 57 (7), 1984, pp. 2023-2024.

Shady Gawad et al., "Impedance Spectroscopy Using Maximum Length Sequences: Application to Single Cell Analysis," Review of Scientific Instruments 78 (5), 2007, pp. 054301-1 to 054301-7.

Arash Soleimani Karimabad and Ralph T. Muehleisen, "Computer Simulations of a Maximum Length Sequence Modulated Photoacoustic Spectrometer," Journal of the Acoustical Society of America 122 (5), 2007.

Ralph T. Muehleisen et al., "Application of Maximum Length Sequences to Photoacoustic Chemical Analysis," Journal of the Acoustical Society of America 121 (5), 2007, pp. 1-16.

Steve Mechels et al., "1D MEMS-Based Wavelength Switching Subsystem," Communications Magazine, Mar. 2003, pp. 88-94, IEEE 41(3).

Ming C. Wu et al., "Optical MEMS for Lightwave Communication, Journal of Lightwave Technology," Dec. 2006, pp. 4433-4454, vol. 24, No. 12.

Michael Vorlander and Malte Kob, "Practical Aspects of MLS Measurements in Building Acoustics," Applied Acoustics, 1997, pp. 239-258, vol. 52, No. 3/4.

Joel Preto Paulo et al., "A Hybrid MLS Technique for Room Impulse Response Estimation," Applied Acoustics 70 (4), 2009, pp. 556-562.

Niranjan Londhe et al., "Application of the ISO 13472-1 in Situ Technique for Measuring the Acoustic Absorption Coefficient of Grass and Artificial Turf Surfaces," Applied Acoustics 70 (1), 2009, pp. 129-141.

Notification of Transmittal of the International Search Report and the Written Opinion of the International Searching Authority, Dec. 21, 2010.

"Jerry Yudelson's Top Ten Green Building Trends for 2009," accessed at http://web.archive.org/web/20101205031039/http://www.sustainablelifemedia.com/content/column/design/top_ten_green_building_trends_for_2009, accessed on Nov. 28, 2012, 4 pages.

Kenji Kato et al., "Correlation Photoacoustics", Chemistry Letters, 1980, pp. 783-786, vol. 9, Issue 7, The Chemical Society of Japan.

James T. Dodgson et al., "Optical-absorption Coefficient Measurements in Solids and Liquids Using Correlation Photoacoustic Spectroscopy", Canadian Journal of Physics, 1986, pp. 1074-1080, vol. 64, No. 9.

\* cited by examiner

PHOTOACOUSTIC SENSOR

CROSS REFERENCE TO RELATED APPLICATION

The present application is a 371 application of the International Application PCT/US2010/054417, filed on Oct. 28, 2010 and entitled "PHOTOACOUSTIC SENSOR."The disclosure of the forgoing application is hereby incorporated by reference in its entirety, including any appendices or attachments thereof, for all purposes.

TECHNICAL FIELD

The present disclosure relates generally to sensor technologies and more specifically a photoacoustic sensor.

BACKGROUND

Unless otherwise indicated herein, the approaches described in this section are not prior art to the claims in this application and are not admitted to be prior art by inclusion in this section.

Gas detection devices are used in numerous applications for detecting the presence of one or more gases, and typically make up part of a system designed to monitor gases that might be harmful to humans or animals. For example, gas detectors are often used to monitor the presence and/or concentration of combustible gases, toxic gases, oxygen, CO2, volatile organic compounds, and the like. One such gas detection device is the photoacoustic gas sensor.

Photoacoustic gas sensors are devices that measure, through acoustic means, optical absorption of different wavelengths of incident light absorbed by a gas. If an amplitude-modulated light source is absorbed by the gas under test, the gas will heat and cool, generating sound energy proportional in amplitude to the optical source and the power absorption coefficient of the gas. By measuring the absorption of light of different wavelengths in this manner, an optical absorption spectrum of the gas is generated and the gas is identified using standard absorption spectroscopy methods. Unlike other spectroscopic systems, which measure absorption optically and have limited sensitivity, photoacoustic systems measure the light energy absorbed by a sample in a completely different manner and can have much higher sensitivity. Some photoacoustic measurement systems are available that can measure in the parts-per-billion (PPB) and even into the parts-per-trillion (PPT) range.

SUMMARY

One embodiment of the disclosure may generally relate to a photoacoustic sensor. The photoacoustic sensor may include an optical modulator configured to modulate an input light beam and produce modulated light that is directed to a sample region; an array of acoustic sensors disposed around the sample region, each of the array of acoustic sensors being substantially equidistant from the sample region, wherein each of the acoustic sensors is adapted to generate a signal responsive to acoustic energy detected in the sample region; and a controller coupled to the acoustic sensors and configured to detect one or more gases present in the sample region based on the signals generated by the acoustic sensors.

Another embodiment of the disclosure may generally relate to a method of detecting one or more gases in a sample. The method may include modulating an input light beam to produce modulated light; directing the modulated light into a region containing the sample; collecting acoustic signals from a plurality of acoustic sensors disposed about the region and substantially equidistant from the region; and evaluating the collected acoustic signals to detect one or more gases present in the sample, wherein the acoustic signals result from interaction of the modulated light with at least a portion of the one or more gases located in the region.

Yet another embodiment of the disclosure may generally relate to a photoacoustic sensor adapted to detect one or more gases from a sample located in a sample region of the photoacoustic sensor. The photoacoustic sensor may include a grating configured to separate an input light beam into wavelength components; a MEMS mirror array configured to modulate the wavelength components to produce modulated light components for the sample region; an acoustic sensor disposed proximate a sample region through which the modulated light components pass and adapted to generate electrical signals responsive to acoustic signals detected in the sample region; and a controller coupled to the acoustic sensors and configured to detect at least a portion of the one or more gases present in the sample region based on the electrical signals generated by the acoustic sensor.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

In the drawings.

DETAILED DESCRIPTION

Figure 1:
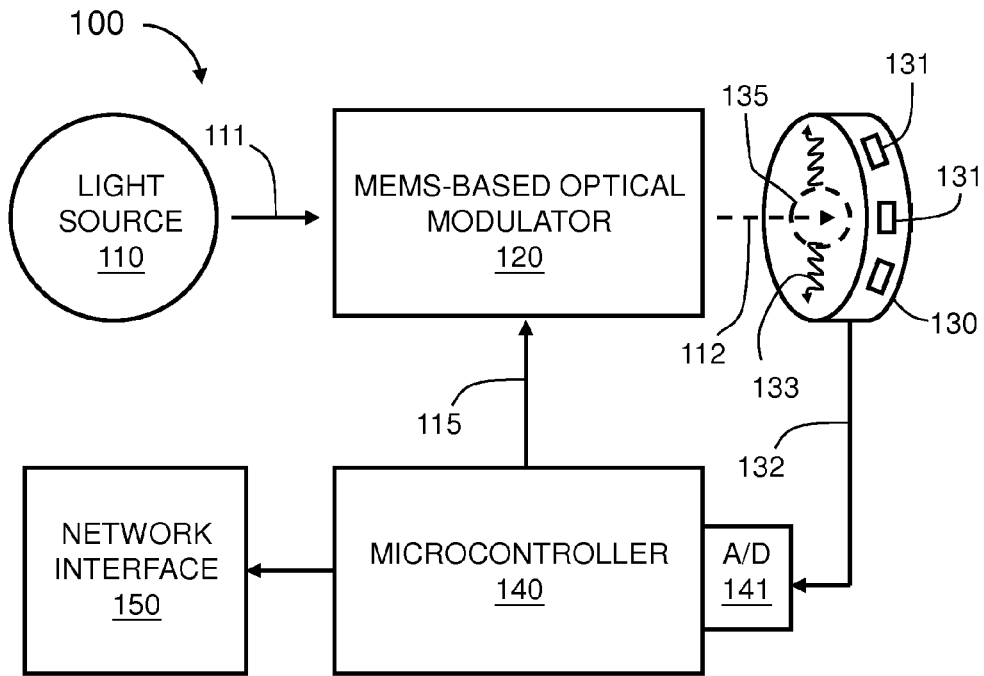
FIG. 1 is a block diagram of a photoacoustic gas sensor.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and systems related to the field of gas detection devices and, in some examples, to air quality micro-sensors.

The present disclosure contemplates conventional photo acoustic systems and identifies that such systems rely on expensive tunable lasers and moving optical components, and thus have significant limitations, including lack of portability, sensitivity to external noise and vibration, the ability to detect only a limited number of chemical compounds, and/or unwieldy size. The present disclosure sets forth further improvements in photoacoustic sensors as described herein. Some embodiments of the present disclosure contemplate apparatus for photoacoustic gas detection, namely a photoacoustic gas sensor that combines a micro-electro-mechanical systems (MEMS) based optical modulator and a ring array of acoustic sensors. The MEMS-based optical modulator can provide flexible wavelength selectivity that may enable the detection of a large number of chemical compounds, and the ring array of acoustic sensors can measure photoacoustically generated acoustic signals without the need for resonant enhancement of a photoacoustic cell of the gas sensor. In some embodiments, a unique, uncorrelated and deterministic signal may be used to modulate each light wavelength of interest. In such embodiments, advanced signal processing may be used that allows the simultaneous measurement of the absorption spectra of multiple optical wavelengths as well as the rejection of unwanted noise that may be detected by the ring array of acoustic sensors.

In some embodiments of the present disclosure, methods of photoacoustic gas detection are described in which a plurality of acoustic sensors may be disposed in an array proximate the sample region of a photoacoustic detector. Each acoustic sensor in the array may be arranged equidistant from the sample region. A broadband light source can be separated into one or more constituent wavelength components, where each of the wavelength components can be modulated and adapted to illuminate a gas sample. The array of acoustic sensors can be adapted to produce an output signal by coherently adding the acoustic signal sensed by each of the acoustic sensors. In one or more embodiments, each of the wavelength components may be modulated by a unique, uncorrelated, and deterministic modulation signal, and the output of the acoustic sensors may be digitized and processed, e.g., with a fast Hadamard transform (HFT), using the modulation signals as the basis functions of the HFTs. In such embodiments, the absorption spectra of multiple optical wavelengths by a gas sample can be determined simultaneously.

FIG. 1 is a block diagram of a photoacoustic gas sensor 100 arranged in accordance with at least some embodiments of the present disclosure. Photoacoustic gas sensor 100 may include a broadband light source 110, a MEMS-based optical modulator 120, a ring array 130 of acoustic sensors 131 disposed around a sample region 135, and a microcontroller 140. In some embodiments, photoacoustic gas sensor 100 may further include a network interface 150 that is adapted for communication with a user.

Broadband light source 110 may be a broadband infrared (IR), visible, or ultra-violet (UV) light source, such as an incandescent, halogen, light emitting diode (LED), or other light source that is adapted to provide a broadband source of light to MEMS-based optical modulator 120. Broadband light source 110 may be configured to direct broadband light 111 to MEMS-based optical modulator 120 using any variety of optical means, such as collimating lenses, mirrors, etc. In some examples, MEMS-based optical modulator 120 may include a diffraction grating and a MEMS optical modulator, each of which are described in greater detail below in conjunction with FIGS. 2A and 2B. In some other examples, MEMS-based optical modulator 120 may be any other array of optical modulators that may be configured to independently modulate the amplitude of multiple input beams. Ring array 130 can be positioned around sample region 135 and aligned with the optical output 112 of MEMS-based optical modulator 120 so that optical output 112 can be directed to sample region 135. Acoustic sensors 131 may be acoustic transducers or some other type of acoustic sensor. Sample region 135 is a cavity configured to contain a desired gas sample for analysis by photoacoustic gas sensor 100. In some embodiments, sample region 135 may be open to the ambient environment to facilitate free-air operation of photoacoustic gas sensor 100. In some other embodiments, sample region 135 may be a closed sampling cell, such as an acoustic cell, into which a sample gas may be pumped. Microcontroller 140 may include an A/D converter 14. The microcontroller 140 is configured to provide modulating signals to MEMS-based optical modulator 120 and can also be adapted to receive, digitize, and post-process signals from acoustic sensors 131. In some examples A/D converter 141 may be external to microcontroller 140, while in some other examples it may be internal to microcontroller 140. Microcontroller 140 can be any appropriate processor including but not limited to general purpose processors such as micro-processors and digital signal processors (DSP), or a special purpose processor such as an application specific integrated circuit (ASIC).

Photoacoustic gas sensor 100 is adapted to measure optical absorption of a gas sample through acoustic means in a manner that may facilitate the detection of one or more chemical compounds simultaneously. In some embodiments, photoacoustic gas sensor 100 may be "chemically agile," i.e., photoacoustic gas sensor 100 may be reprogrammed to monitor different chemical compounds with no changes in hardware configuration required. Further, in some embodiments, photoacoustic signals produced by a gas sample being tested by photoacoustic gas sensor 100 may be generated using unique modulation signals for each wavelength of absorbed light, and may undergo signal processing that may enable the absorption spectra of multiple optical wavelengths by a gas sample to be determined simultaneously. Such modulation signals and signal processing are described in greater detail below in conjunction with FIGS. 2A and 2B.

When photoacoustic gas sensor 100 is in operation, broadband light source 110 directs broadband light 111 to MEMS-based optical modulator 120 using optical means such as focusing lenses, mirrors, etc., so that broadband light 111 enters MEMS-based optical modulator 120 as required. MEMS-based optical modulator 120 is adapted to receive and separate broadband light 111 into multiple wavelength components and can selectively perform binary amplitude modulation, i.e., on/off modulation, of one or more desired wavelength components thereof. The number of desired wavelength components into which broadband light 111 is separated by MEMS-based optical modulator 120 may be on the order of tens, hundreds, or even thousands, depending on the number and type of chemical compounds that photoacoustic gas sensor 100 is configured to detect. Broadband light 111 can be separated into such a large number of wavelength components because MEMS-based optical switch 120 may include a diffraction grating configured to spatially separate broadband light 111 into wavelength components and a MEMS mirror array configured to selectively perform binary modulation of any desired wavelength component or components. MEMS-based optical modulator 120 can output a modulated light beam 112, which then can pass through a gas sample disposed in sample region 135. Different wavelengths of light can be absorbed by the one or more gases making up the gas sample and, by means of the photoacoustic effect, sound waves 133 may be generated by the gas sample. Acoustic sensors 131 of ring array 130 are adapted to sense and convert sound waves 133 to sensor output 132, which can be coupled to microcontroller 140 for signal processing. Ring array 130 may be configured to enhance the acoustic signal of sound waves 133 received by acoustic sensors 131 and reduce the acoustic signal of unwanted noise by acoustic sensors 131 by using coherent addition. The configuration of ring array 130 and the use of coherent addition of sensor output 132 is described in greater detail below in conjunction with FIG. 3. Microcontroller 140 can be arranged to receive and digitize sensor output 132 via A/D converter 141 and may also be arranged to perform the necessary digital signal processing to determine the absorption amplitudes of a gas sample for one or more desired wavelengths. In addition, microcontroller 140 may be configured to provide modulation signals 115 to MEMS-based optical modulator 120, where modulation signals 115 may be unique, uncorrelated and deterministic signals configured so that MEMS-based optical modulator 120 performs binary modulation of the amplitude of one or more incident wavelength components in a pattern that is unique for each wavelength component. In one embodiment, microcontroller 140 is configured to interface with MEMS-based optical switch 120 through a serial or parallel digital interface.

Photoacoustically generated sound waves 133 are generated as a function of the modulation frequency of wavelength components 126 absorbed by a gas sample in sample region 135. Because there is generally very little ambient noise present in the ultra-sonic range, i.e., at sound frequencies greater than about 20 kHz, in some embodiments the frequency of the modulation signals 115 applied to MEMS-based optical modulator 120 may be selected to be in the ultrasonic range. In this way, the acoustic signal produced by sounds waves 133 may have a more favorable signal-to-noise ratio relative to the signal-to-noise ratio of sound waves 133 produced by lower frequency modulation signals 115. In some examples, MEMS mirrors can operate in the kHz regime, i.e., the frequency at which individual MEMS mirrors in MEMS-based optical modulator 120 can be changed from the binary "on" to the binary "off" position (and vice-versa) can be less than one thousandth of a second. Thus, MEMS-based optical modulator 120 can be used to modulate wavelength components 126 in the ultra-sonic regime as needed.

Figure 2A:
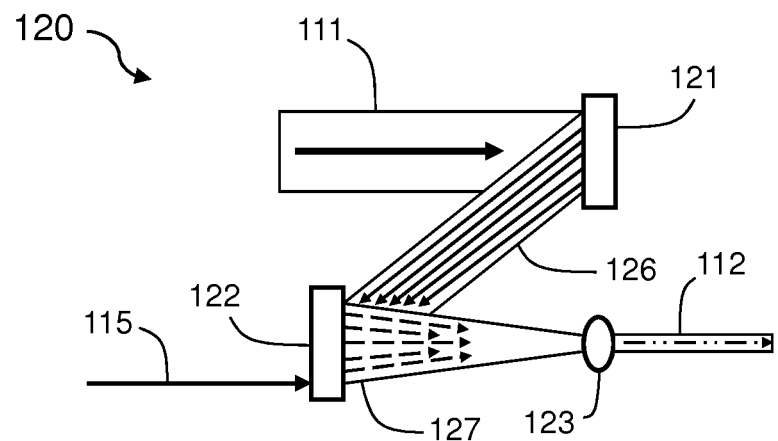
FIG. 2A is a schematic diagram of one configuration of micro-electro-mechanical systems (MEMS) based optical modulator.

FIG. 2A is a schematic diagram of one configuration of MEMS-based optical modulator 120, arranged according to one or more embodiments of the disclosure. As shown, MEMS-based optical modulator 120 is configured to receive broadband light 111 from broadband light source 110 (shown in FIG. 1) and is adapted to direct optical output 112 to sample region 135 (shown in FIG. 1). MEMS-based optical modulator 120 may include a dispersive element 121, a MEMS mirror array 122, and one or more optical components represented by collimating element 123. Additional optical components that may facilitate the operation of MEMS-based optical modulator 120 may include one or more of collimating optics, focusing lenses, mirrors, optical filters, pinholes, polarizing elements, blocking elements, etc., and are not shown for clarity.

Dispersive element 121 may be any light-diffracting optical device known in the art for separating broadband light 111 into one or more wavelength components 126, such as a diffraction grating, a prism, an arrayed waveguide grating, etc. MEMS mirror array 122 may be an array of multiple MEMS micro-mirrors, which may include tens, hundreds, or even thousands of micro-mirrors. Each micro-mirror may be configured to direct incident light, i.e., one of wavelength components 126, along one of two optical paths. When commanded to modulate an incident wavelength component 126 in the binary "on" state, a micro-mirror directs the incident wavelength component 126 to collimating element 123. When commanded to modulate an incident wavelength component 126 in the binary "off" state, the micro-mirror directs the incident wavelength component 126 to a light dump or other light-absorbing device. Each micro-mirror of MEMS mirror array 122 may be independently controlled by microcontroller 140; therefore MEMS mirror array 122 may be configured to independently modulate the optical intensity of a plurality of incident beams, such as the wavelength components 126. Collimating element 123 may include one or more fixed optical elements, such as lenses and/or mirrors, positioned to collimate incident light to produce optical output 112, where optical output 112 may be a collimated and wavelength-modulated light beam.

Figure 2B:
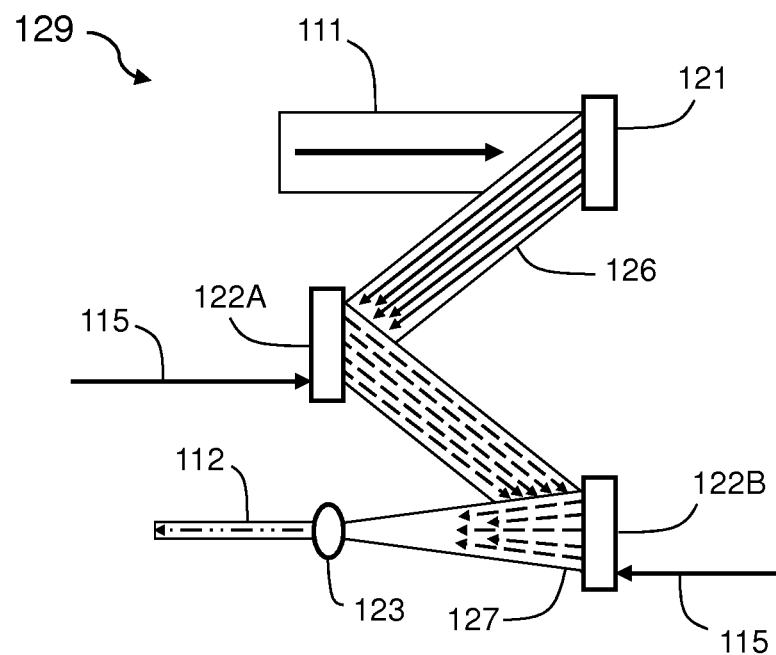
FIG. 2B is a schematic diagram of another configuration of MEMS-based optical modulator.

FIG. 2B is a schematic diagram of another configuration of MEMS-based optical modulator 129, arranged according to one or more embodiments of the disclosure. As shown, MEMS-based optical modulator 129 is substantially similar to MEMS-based optical modulator 120 except that the former includes a first MEMS mirror array 122A and a second MEMS mirror array 122B. In such an embodiment, first MEMS mirror array 122A and a second MEMS mirror array 122B may each receive the same modulation signals 115 from microprocessor 140 (shown in FIG. 1). MEMS-based optical modulator 129 is configured so that the optical intensity of each wavelength component 126 may undergo binary modulation by first MEMS mirror array 122A and an identical binary modulation by second MEMS mirror array 122B. In this way, the double MEMS mirror configuration of MEMS-based optical modulator 129 provides deeper modulation amplitude, i.e., the optical contrast between the binary "on" and "off" states is enhanced for each wavelength component 126.

Figure 2C:
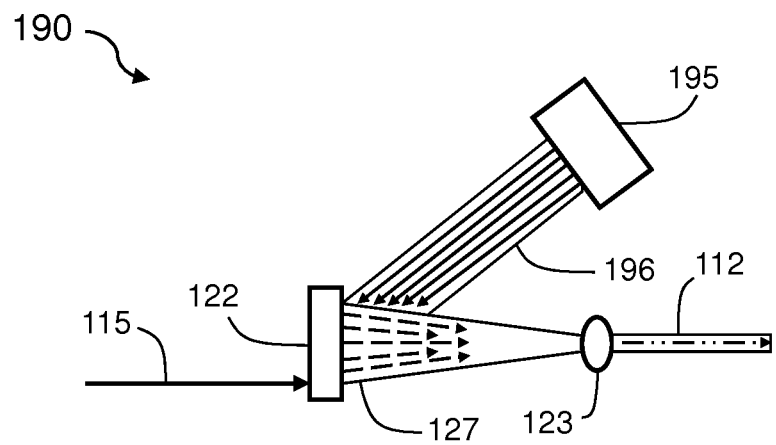
FIG. 2C is a schematic diagram of a MEMS-based optical modulator having one or more narrowband light sources instead of a broadband light source.

FIG. 2C is a schematic diagram of a configuration of a MEMS-based optical modulator 190 having one or more narrowband light sources 195 instead of a broadband light source, in accordance with at least some embodiments described herein. Narrowband light source 195 may be one or more fixed and/or tunable lasers, diodes, filtered LEDs, or other narrowband light sources. Because narrowband light 196 is already divided into one or more discrete light bands, dispersive element 121 is not required for the proper operation of MEMS-based optical modulator 190. Narrowband light 196 can be modulated by MEMS mirror array 122 in the same manner that wavelength components 126 are modulated by MEMS mirror array 122 as described below. In MEMS-based optical modulator 190, narrowband light 196 may be optically combined prior to incidence on MEMS mirror array 122.

Figure 2D:
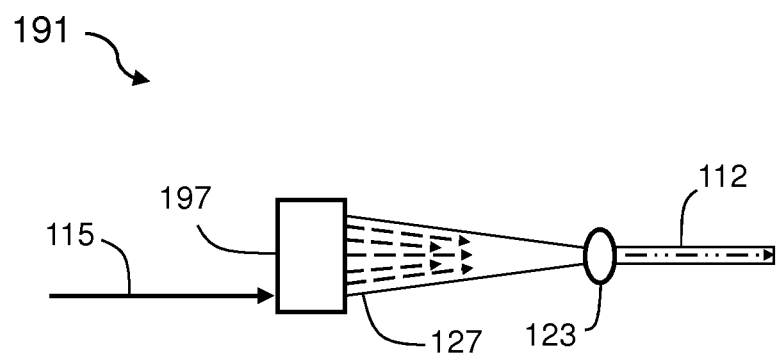
FIG. 2D is a schematic diagram of a configuration of a narrowband light source having an array of modulated narrowband light sources instead of a broadband light source, dispersive element, and MEMS mirror array.

FIG. 2D is a schematic diagram of a configuration of a modulated narrowband light source 191 having an array 197 of modulated narrowband light sources instead of a broadband light source, dispersive element 121, and MEMS mirror array 122, in accordance with at least some embodiments described herein. The narrow band light sources making up array 197 may include one or more tunable lasers, diodes, filtered LEDs, or other narrowband light sources that can be modulated as described below at frequencies in the kHz regime or higher. For example, a laser diode may be configured to modulate by modulating power that is supplied to the diode, an LED can be configured to modulate by modulating the current flow through the LED, etc. The operation of modulated narrowband light source 191 is substantially similar to that of MEMS-based optical modulator 120, described below, except that the individual frequency components are modulated directly and therefore do not require MEMS mirror array 122 for modulation.

In operation, MEMS-based optical modulator 120 is adapted to receive and divide broadband light 111 into wavelength components 126, which are directed to MEMS mirror array 122 as shown. MEMS mirror array 122 receives wavelength components 126 and selectively modulates one or more desired wavelength components based on modulation signals 115 directed thereto from microcontroller 140. Wavelength components 126 are spatially separated from each other by dispersive element 121 such that each of wavelength components 126 is directed to a different portion of MEMS mirror array 122. Since each of the individual mirrors in MEMs mirror array 122 can be operated independently from one another, each of wavelength components 126 can be modulated independently from one another. The particular wavelength components that are modulated by MEMS mirror array 122 are a function of what particular chemical compounds photoacoustic gas sensor 100 is configured to detect, since the absorption spectrum is different for every chemical compound. Consequently, when photoacoustic gas sensor 100 is configured to monitor a relatively small number of gases and/or chemical compounds, the optical absorption of a few wavelength components may be required in order to quantify the concentration of the gases and chemical compounds. Conversely, when photoacoustic gas sensor 100 is configured to monitor a large number of gases and/or chemical compounds, the number of absorption spectra of the gas to be determined increases accordingly. In either case, the modulated wavelength components 127 can then be collimated and directed to sample region 135 by collimating element 123.

In some embodiments, modulation signals 115 may be selected to produce modulation of the one or more desired wavelength components in a manner substantially similar to conventional photoacoustic sensors, i.e., a "chopped" light beam for a single wavelength component can be produced and passed through a gas sample to produce an acoustic signal via the photoacoustic effect. In such embodiments, each wavelength of light to be photoacoustically tested for absorption by photoacoustic gas sensor 100 can be measured individually. Unlike some photoacoustic sensors that rely on one or more tunable lasers, photoacoustic gas sensor 100 is "wavelength agile," and may generate and modulate each desired wavelength of light individually by using dispersive element 121 in conjunction with MEMS mirror array 122. Specifically, dispersive element 121 can be configured to spatially separate the wavelength components that make up broadband light 111, and MEMS mirror array 122 can be adapted to direct a particular wavelength component of interest to MEMS mirror array 122 and all other wavelength components to a light dump or other light-absorbing device. The chopped light beam, which is made up of the wavelength component of interest, can then be passed through the gas sample and the optical absorption of the gas sample for the particular wavelength component of interest can be determined by measuring sound waves 133 with acoustic sensors 131. A distinct advantage of such an approach is that in lieu of a tunable laser, a much less complex light source may be used, i.e., a broadband visible, IR, or UV light source.

In some embodiments, modulation signals 115 may be selected to modulate the amplitude of the one or more desired wavelength components in a way that enables microcontroller 140 to determine the absorption spectra of multiple chemical compounds simultaneously. In such embodiments, photoacoustic signals produced by a gas sample may be generated using unique, uncorrelated, and deterministic modulation signals for each wavelength of light that is absorbed by the gas or chemical compound being monitored. Thus, modulation signals 115 may be made up of a plurality of uncorrelated and deterministic modulation signals, one for each wavelength component 126 of interest, an approach that differs significantly from known techniques for modulating light in prior art photoacoustic sensors, e.g., simple light pulses, simple binary on/off chains, or sinusoidal modulation of light source amplitude.

Each uncorrelated and deterministic modulation signal can be applied to the appropriate mirror or mirrors of MEMS mirror array 122 to modulate a corresponding wavelength component of broadband light 111. Thus, referring to FIGS. 1 and 2A, when modulated wavelength components 127 are directed to sample region 135 to produce sound waves 133, microcontroller 140 can receive the acoustic signal via acoustic sensors 131 and digitize the acoustic signal with A/D converter 141. Microcontroller 140 can then extract the absorption spectra for the gases being monitored by using correlation analysis based on the uncorrelated modulation signals, where the optical absorption of each wavelength component by the gas sample is individually determined from the acoustic signal. In other words, for each modulated wavelength component 127 being absorbed by the gas sample, correlation analysis may be used to correlate the output (sound waves 133) with the input modulating signal applied to each light wavelength, where the amplitude (or magnitude) of the correlation indicates the amount of absorption of each modulated wavelength component 127 that generated sound waves 133. In some embodiments, Fast Hadamard transforms (FHTs), fast Fourier transforms (FFTs), and the like may be applied to the digitized acoustic signal to perform such correlation analysis. In such embodiments, microcontroller 140 uses modulation signals 115 as the basis functions for the correlation analysis, so that the different outputs of the FHTs, FFTs, etc., are impulse responses of the system, at each wavelength of interest, where the "system" in this case is defined as photoacoustic gas sensor 100. Thus, the correlation amplitude of each FHT (or FFT or other analysis method) indicates the amount of light at the wavelength of interest that is absorbed by the gas sample. Microcontroller 140 performs such correlation analysis for each modulation signal 115 that is applied to MEMS-based optical modulator 120 by applying an FHT (or FFT or other analysis method) to the digitized acoustic signal to produce an impulse response at the wavelength of light being modulated by the particular modulation signal 115. In such an embodiment, the correlation analysis method (FHT, FFT, etc.) uses the particular modulation signal 115 as its basis function. Each of the resultant impulse responses is proportional to the optical absorption coefficient of the sample gas at a particular wavelength of light, which microprocessor 140 can use to construct the desired absorption spectra for any gas being monitored. It is noted that the relative peak amplitude of such impulse responses, rather than the absolute value of such impulse responses, may be best suited for determining absorption spectra since the constant of proportionality depends at least in part on the specific sensors and light source being used and is not always easily determined.

In some embodiments, the unique, deterministic, uncorrelated modulation signals 115 that are applied to wavelength components 126 of interest and are used as the basis functions of correlation analysis may be based on a pseudo-random binary sequence (PRBS). Since different members of the PRBS series are substantially uncorrelated, the selection of each deterministic, uncorrelated modulation signal 115 applied to each wavelength may be simplified by the use of PRBSs. In one embodiment, the particular PRBS used for each of modulation signals 115 applied to wavelength components 126 may be a maximum length sequence (MLS). An advantageous feature of MLS-based signals for such an embodiment is that MLS-based signals have the property of orthogonality, i.e., the autocorrelation of MLS-based signals is nearly a perfect unit impulse while the cross-correlation of MLS-based signals is zero. Thus, the correlation of an MLS-modulated sensor signal, i.e., sensor output 132, is the impulse response of the measurement system to the stimulus signal. Specifically, the orthogonality of MLS-modulated modulation signals 115 dictates that the impulse response, i.e., the output of a single FHT, FFT, etc., that uses one of modulation signals 115 as a basis function, is a measure of system response at the particular light wavelength that has been modulated. The amplitude of that impulse response, which represents the total energy in the impulse response system, is proportional to the amount of absorbed light at that particular wavelength. This provides the amount of absorbed light at each wavelength of interest, so microprocessor 140 can then readily construct the desired absorption spectra for any gas being monitored. Thus, the use of MLS-based signals to modulate wavelength components 126 in photoacoustic gas sensor 100 enables microprocessor 140 to efficiently extract and separate light absorption of each wavelength by a gas sample simultaneously, which enables monitoring of multiple gases. For example, microprocessors and other electronics may be adapted to provide a modulation rate on the order of 100 kHz for modulation signals 115, which means that a single measurement having a signal length of $2^{20}$ can be completed in approximately 10 seconds (i.e., $2^{20}/100$ kHz≈10 seconds) where each measurement quantifies the concentration of a large number of gases and chemical compounds, e.g., tens, hundreds, or even thousands. Thus, photoacoustic gas sensor 100 can monitor a large number of gases and chemical compounds continuously.

For photoacoustic sensors to achieve high sensitivity, elimination of acoustic noise is required. Some photoacoustic sensors rely on the use of a sealed acoustic cell that is also configured to be an acoustic resonator. Embodiments of the present disclosure may reduce the impact of external acoustic noise via the application of multiple deterministic and uncorrelated signals and signal processing methods described above and also through the use of a ring array of acoustic sensors. Because PRBS and MLS signals are deterministic, i.e., repeatable, external noise added to sound waves 133 and incorporated into sensor output 132 may be effectively removed by synchronously averaging multiple measurement sequences in some manner. In one embodiment, the measures signals are averaged prior to correlation analysis. In another embodiment, the correlation analysis can be performed on all signals and then averaged. In addition, the amount of external noise added to sound waves 133 may be minimized by configuring a plurality of acoustic sensors according to embodiments of the present disclosure.

Figure 3:
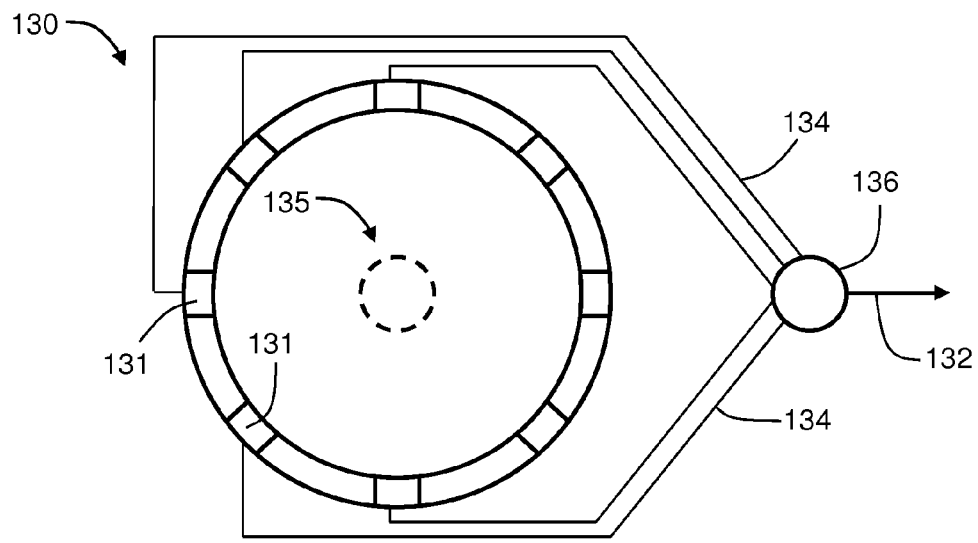
FIG. 3 is a schematic diagram of one configuration of acoustic sensors disposed around a sample region.

FIG. 3 is a schematic diagram of one configuration of acoustic sensors disposed around a sample region, in accordance with one or more embodiments of the present disclosure. As shown, ring array 130 may include a plurality of acoustic sensors 131 mounted thereto and disposed around sample region 135. It is emphasized that while the internal volume of ring array 130 may contain sample gases, sample region 135 is defined as containing the portion of sample gas through which a modulated light beam passes, such as modulated light beam 112. Acoustic sensors 131 are mounted to (or integrally formed with) ring array 130 so that each acoustic sensor is disposed substantially equidistant from sample region 135. In addition, the outputs 134 of acoustic sensors 131 are directly added by electronic circuit 136 to be combined into a sensor output 132. The means by which outputs 134 are combined, (e.g., voltage output, current output, variable capacitance, variable inductance, and the like), depends on the particular acoustic sensor being used. In some embodiments, acoustic sensors 131 may be voltage output microphones which are added with an analog summation circuit 136 to produce sensor output 132. In some alternative embodiments, the output signal from each acoustic sensor 131 may be digitized separately and then combined via a beam-forming algorithm in a digital circuit or by microcontroller 140. In yet other embodiments, the acoustic sensors 131 could incorporate A/D converters in their assemblies, in which case the digitized data is combined via a beam-forming algorithm in a digital circuit or by microcontroller 140.

In some embodiments, ring array 130 can be made up of pairs of acoustic sensors 131, each pair of sensors being disposed in line with and substantially equidistant from sample region 135. Such an embodiment is illustrated in FIG. 3. In other embodiments, ring array 130 is made up of acoustic sensors 131 that are not disposed in pairs directly opposite each other. In other embodiments, ring array 130 can be made of a single cylindrically shaped acoustic sensor. In one embodiment, so long as acoustic sensors 131 are each substantially equidistant from sample region 135, the output of the ring array 130 can be maximized for sound sources inside sample region 135 and may be significantly reduced for sound sources originating elsewhere, i.e., unwanted acoustic noise. Thus, if modulated light beam 112 is directed through sample region 135, the photoacoustic signal output may be increased and the output of acoustic noise decreased (i.e., increased signal to noise (S/N) ratio). The increase in photoacoustic signal output is due to coherent addition of the signals generated by each of acoustic sensors 131. Coherent addition of the output signals of acoustic sensors 131 takes place because each of acoustic sensors 131 is equidistant from the sound source, which means that the signal from any acoustic source in sample region 135 is coherent in, i.e., in phase with, each of acoustic sensors 131.

For N sensors, coherent addition of the outputs of acoustic sensors 131 provides an $N^2$ increase in the power of the output signal of an acoustic source positioned in sample region 135. Thus, for N=8, a gain of almost 20 dB is provided even though ring array 130 is not configured as an acoustic resonator. Because of this, a ring array arranged according to one or more embodiments of the present disclosure may significantly reduce the effect of acoustic noise in any photoacoustic gas sensor. The beneficial effects of ring array 130 may be further increased by configuring photoacoustic gas sensor 100 with multiple ring arrays 130, each of which including a plurality of acoustic sensors 131.

Figure 4:
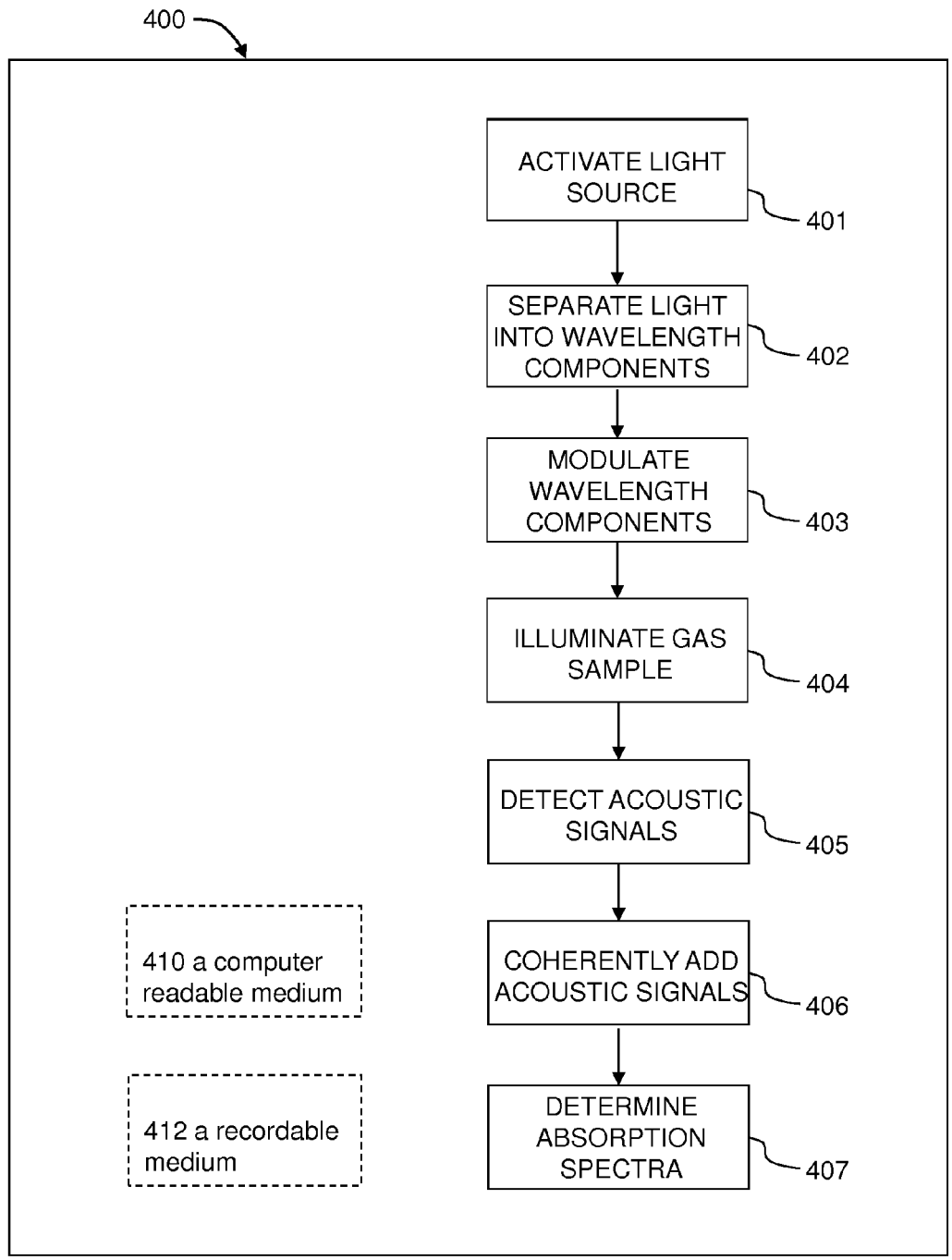
FIG. 4 sets forth a flow chart summarizing a method of photoacoustic gas detection.

FIG. 4 sets forth a flow chart summarizing a method 400 of photoacoustic gas detection, according to at least some embodiments of the present disclosure. For ease of description, method 400 is described in terms of a photoacoustic sensor substantially similar to photoacoustic gas sensor 100 in FIG. 1. However, other configurations of photoacoustic sensor may also perform method 400. Method 400 may include one or more functions, operations, or actions as depicted by blocks 401, 402, 403, 404, 405 and/or 406. In some implementations, the various features of the illustrated blocks for method 400 may be combined into fewer blocks, divided into additional blocks, or eliminated based on the desired result. Processing for method 400 may begin at block 401.

Processing for method 400 may begin at block 401 "activate light source." Block 401 may be followed by block 402, "separate light into wavelength components." Block 402 may be followed by block 403, "modulate wavelength components." Block 403 may be followed by block 404, "illuminate gas sample." Block 404 may be followed by block 405, "detect acoustic signals." Block 405 may be followed by block 406, "coherently add acoustic signals." Block 406 may be followed by block 407, "determine absorption spectra."

In block 401, "activate light source", broadband light source 110 is activated by microcontroller 140 and directs broadband light 111 to MEMS-based optical modulator 120.

In block 402, "separate light into wavelength components", broadband light 111 may be separated into one or more constituent wavelength components 126. In at least some embodiments, a diffraction grating is used to separate the broadband light source.

In block 403, "modulate wavelength components", one or more of wavelength components 126 may be binary amplitude modulated to produce modulated wavelength components 127. In at least some embodiments, MEMS mirror array 122, controlled by microcontroller 140, may be used to perform the modulation of the individual wavelength components 126. In at least some embodiments, wavelength components 126 that are modulated may be selected to coincide with frequencies of light that are absorbed by one or more gases to be monitored by photoacoustic gas sensor 100. In one embodiment, the modulation signal 115 for each wavelength component 126 to be modulated may be unique with respect to the modulation signals applied to each of the other wavelength components 126. In such an embodiment, the modulation signal 115 may be a PRBS-based modulation signal, such as an MLS-based modulation signal.

In block 404, "illuminate gas sample", a gas sample may be illuminated in the sample region by one or more of the modulated wavelength components 127 produced in block 403 so that an acoustic signal in sample region 135, i.e., sound waves 133, may be produced by means of the photoacoustic effect.

In block 405, "detect acoustic signals", acoustic sensors 131 may detect sound waves 133 produced in sample region 135.

In block 406, "coherently add acoustic signals", ring array 130 of acoustic sensors 131 may produce sensor output 132 by coherently adding the acoustic signal sensed by each of acoustic sensors 131 using electronic summation device 136. The summation process may be a digital summation process or an analog summation process.

In block 407, "determine absorption spectra", microprocessor 140 may be adapted to determine the appropriate absorption spectra based on the summed sensor output 132. As described above in conjunction with FIGS. 2A, 2B, microcontroller 140 evaluates the digitized version of the summed signals and extracts the absorption spectra for the gases being monitored by using correlation analysis based on the uncorrelated modulation signals 115. In embodiments in which modulation signals 115 are PRBS-based or MLS-based modulation signals, microprocessor 140 may (in some examples) digitize and process sensor output 132 with FHTs, using modulation signals 115 as the basis functions for the FHTs.

A computer program product may include one or more sets of executable instructions for executing the method 400 described above and illustrated in FIG. 4. The computer program product may be recorded in a computer readable medium 410 or another similar recordable medium 412.

Figure 5:
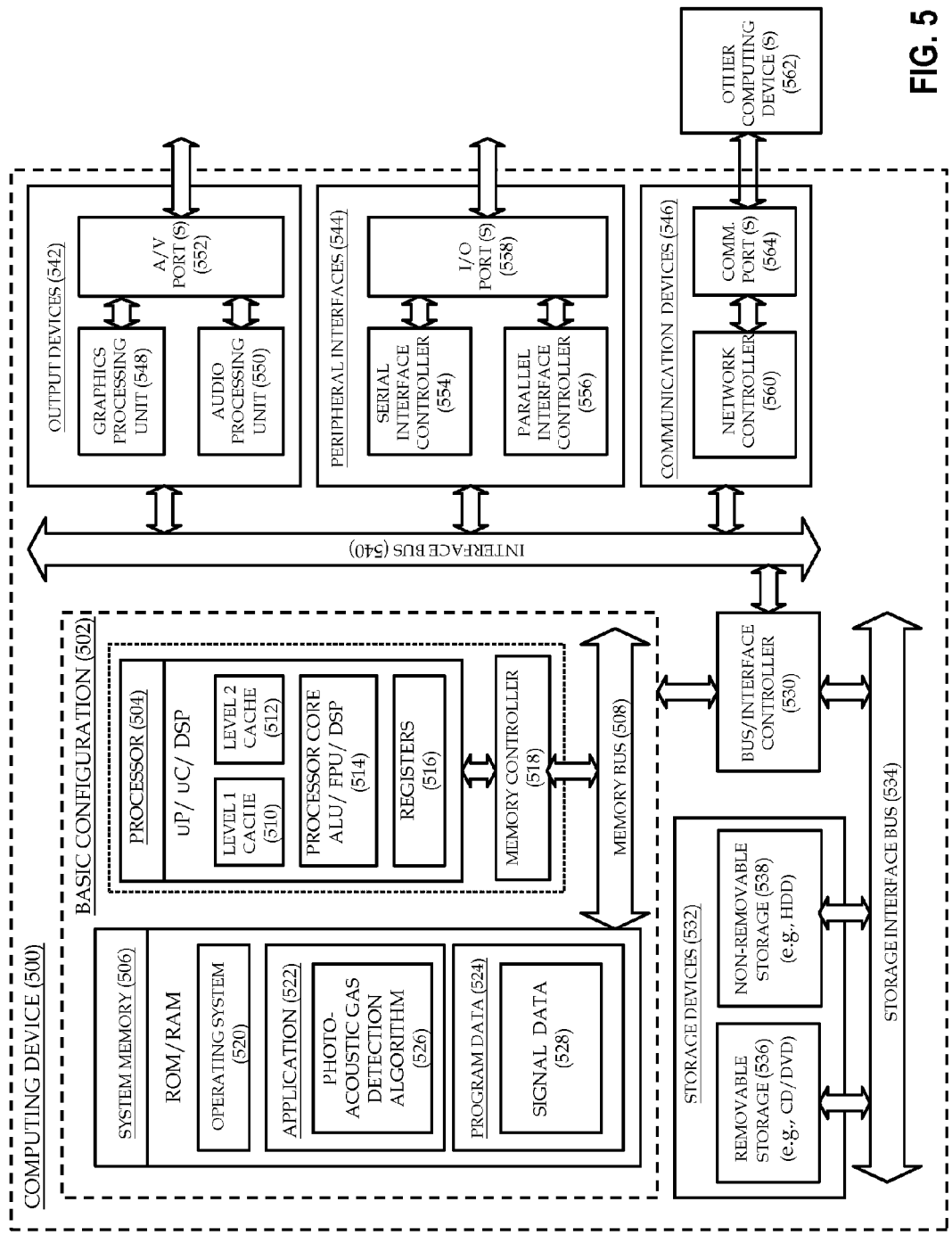
FIG. 5 is a block diagram illustrating an example computing device that is arranged for detecting one or more gases in a sample; all arranged in accordance with at least some embodiments of the present disclosure.

FIG. 5 is a block diagram illustrating an example computing device 500 that is arranged for detecting one or more gases in a sample, according to at least some embodiments of the present disclosure. In a very basic configuration 502, computing device 500 typically includes one or more processors 504 and a system memory 506. A memory bus 508 may be used for communicating between processor 504 and system memory 506.

Depending on the desired configuration, processor 504 may be of any type including but not limited to a microprocessor (µP), a microcontroller (µC), a digital signal processor (DSP), or any combination thereof. Processor 504 may include one more levels of caching, such as a level one cache 510 and a level two cache 512, a processor core 514, and registers 516. An example processor core 514 may include an arithmetic logic unit (ALU), a floating point unit (FPU), a digital signal processing core (DSP Core), or any combination thereof. An example memory controller 518 may also be used with processor 504, or in some implementations memory controller 518 may be an internal part of processor 504.

Depending on the desired configuration, system memory 506 may be of any type including but not limited to volatile memory (such as RAM), non-volatile memory (such as ROM, flash memory, etc.) or any combination thereof. System memory 506 may include an operating system 520, one or more applications 522, and program data 524. Application 522 may include a photoacoustic gas detection algorithm 526 that is arranged to perform the functions as those described with respect to method 400 of FIG. 4. Program data 524 may include signal data 528 that may be useful for operation with photoacoustic gas detection algorithm 526 as is described herein. In some embodiments, application 522 may be arranged to operate with program data 524 on operating system 520. This described basic configuration 502 is illustrated in FIG. 5 by those components within the inner dashed line.

Computing device 500 may have additional features or functionality, and additional interfaces to facilitate communications between basic configuration 502 and any required devices and interfaces. For example, a bus/interface controller 530 may be used to facilitate communications between basic configuration 502 and one or more data storage devices 532 via a storage interface bus 534. Data storage devices 532 may be removable storage devices 536, non-removable storage devices 538, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 506, removable storage devices 536 and non-removable storage devices 538 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of computing device 500.

Computing device 500 may also include an interface bus 540 for facilitating communication from various interface devices (e.g., output devices 542, peripheral interfaces 544, and communication devices 546) to basic configuration 502 via bus/interface controller 530. Example output devices 542 include a graphics processing unit 548 and an audio processing unit 550, which may be configured to communicate to various external devices such as a display or speakers via one or more A/V ports 552. Example peripheral interfaces 544 include a serial interface controller 554 or a parallel interface controller 556, which may be configured to communicate with external devices such as input devices (e.g., keyboard, mouse, pen, voice input device, touch input device, etc.) or other peripheral devices (e.g., printer, scanner, etc.) via one or more I/O ports 558. An example communication device 546 includes a network controller 560, which may be arranged to facilitate communications with one or more other computing devices 562 over a network communication link via one or more communication ports 564.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 500 may also be implemented as a personal computer including both laptop computer and non-laptop computer configurations.

In sum, one or more embodiments of the disclosure may provide a portable and self-contained photoacoustic sensor capable of free-air operation and high sensitivity. Portability can be facilitated by reduced size, from use of MEMS optical systems and an on-board microcomputer, and the elimination of gas sampling and piping found in typical photoacoustic systems. In addition, photoacoustic sensors arranged according to one or more embodiments of the present disclosure may have sensitivities in the parts-per-million (PPM) or even the PPB level, while providing data collection speeds on par with conventional photoacoustic detectors—even when a large number of gases is being monitored. Further, due to the "wavelength agile" properties of MEMS-mirror-based optical modulators, photoacoustic sensors arranged according to one or more embodiments of the present disclosure may also be readily reprogrammed to monitor different gases and chemical compounds with no changes in hardware. Thus, photoacoustic sensors arranged according to one or more embodiments of the present disclosure provide the portability and selectivity of existing miniature near infrared and optical MEMS spectrometers, the sensitivity and speed of conventional photoacoustic detectors, and the convenience of free-air operation.

In addition, photoacoustic sensors as described herein may be adapted to measure the optical absorption of the surfaces of solids and/or liquids. In such embodiments, the wavelength-modulated output from the MEMS-based optical modulator could be split into two beams, one of which would be directed towards the surface of a solid or liquid. A second set of sensors would measure the acoustic signal reradiated from the solid/liquid surface. A comparison between the air sensor output and the solid/liquid sensor output would isolate the absorption of the solid/liquid from the air immediately in front of the solid/liquid.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A photoacoustic sensor comprising:
an optical modulator configured to modulate an input light beam and produce modulated light that is directed to a sample region;
an array of acoustic sensors disposed in a ring configuration around the sample region, each of the array of acoustic sensors being substantially equidistant from the sample region, wherein each of the acoustic sensors is adapted to generate a signal responsive to acoustic enemy detected in the sample region; and
a controller coupled to the acoustic sensors and configured to detect one or more gases present in the sample region based on the signals generated by the acoustic sensors.

2. The photoacoustic sensor of claim 1, wherein the controller is coupled to the optical modulator and adapted to control the modulation of the input light beam.

3. The photoacoustic sensor of claim 1, wherein the optical modulator comprises a dispersive element configured to separate the input light beam into wavelength components and is also configured to modulate the wavelength components non-uniformly.

4. The photoacoustic sensor of claim 1, wherein the optical modulator comprises a grating configured to separate the input light beam into wavelength components and is also configured to modulate the wavelength components non-uniformly.

5. The photoacoustic sensor of claim 1, wherein the optical modulator comprises a MEMS mirror array that is adapted to modulate the input light beam.

6. The photoacoustic sensor of claim 1, wherein the optical modulator comprises a first MEMS mirror array adapted to modulate a first wavelength component of the input light beam and a second MEMS mirror array adapted to modulate the same wavelength component of the input light beam.

7. The photoacoustic sensor of claim 1, wherein the optical modulator comprises one or more narrowband light sources, and a MEMS mirror array for modulating narrowband light from the one or more narrowband light sources to produce the modulated light that is directed to the sample region.

8. The photoacoustic sensor of claim 1, wherein the optical modulator comprises an array of modulated narrowband light sources that produces the modulated light that is directed to the sample region.

9. A method of detecting one or more gases in a sample, the method comprising:
   modulating an input light beam by separating the input light beam into wavelength components and modulating each of the wavelength components non-uniformly to produce modulated light;
   directing the modulated light into a region containing the sample:
   collecting acoustic signals from a plurality of acoustic sensors disposed about the region and substantially equidistant from the region; and
   evaluating the collected acoustic signals to detect one or more gases present in the sample, wherein the acoustic signals result from interaction of the modulated light with at least a portion of the one or more gases located in the region.

10. The method of claim 9, further comprising digitizing the acoustic signals, wherein the one or more gases detected in the sample are detected by evaluating the digitized acoustic signals.

11. The method of claim 9, wherein one or more of modulating, directing, collecting, and/or detecting are carried out by a photoacoustic sensor having an optical modulator, an array of acoustic sensors, and a controller.

12. The method of claim 9, wherein the modulated light is produced by an array of modulated narrowband light sources.

13. A method of detecting one or more gases in a sample, the method comprising:
   modulating a first wavelength component of an input light beam using a first deterministic mudulation signal and modulating a second wavelength component of the input light beam using a second deterministic modulation signal to produce modulated light wherein the first deterministic modulation signal and the second deterministic modulation signal are uncorrelated to each other;
   directing the modulated light into a region containing the sample;
   collecting acoustic signals from a plurality of acoustic sensors disposed about the region and substantially equidistant from the region; and
   evaluating the collected acoustic signals to detect one or more gases present in the sample, wherein the acoustic signals result from interaction of the modulated light with at least a portion of the one or more gases located in the region.

14. A method of detecting one or more gases in a sample, the method comprising:
   modulating an input light beam to produce modulated light, wherein the input light beam is generated from one or more narrowband light sources, and modulated with a MEMS mirror array;
   directing the modulated light into a region containing the sample;
   collecting acoustic signals from a plurality of acoustic sensors disposed about the region and substantially equidistant from the region; and
   evaluating the collected acoustic signals to detect one or more gases present in the sample, wherein the acoustic signals result from interaction of the modulated light with at least a portion of the one or more gases located in the region.

15. A photoacoustic sensor adapted to detect one or more gases from a sample located in a sample region of the photoacoustic sensor, the photoacoustic sensor comprising:
   a grating configured to separate an input light beam into wavelength components;
   a MEMS mirror array configured to modulate the wavelength components to produce modulated light components for the sample region;
   an acoustic sensor disposed proximate a sample region through which the modulated light components pass and adapted to generate electrical signals responsive to acoustic signals detected in the sample region; and
   a controller coupled to the acoustic sensor and configured to detect at least a portion of the one or more gases present in the sample region based on the electrical signals generated by the acoustic sensor.

16. The photoacoustic sensor of claim 15, the MEMS mirror array comprising a first MEMS mirror array and a second MEMS mirror array, wherein the first MEMS mirror array is configured to modulate a first set of the wavelength components, and wherein the second MEMS mirror array is configured to modulate a second set of the wavelength components.

17. The photoacoustic sensor of claim 15, wherein the controller is adapted to provide a unique uncorrelated deterministic modulation signal to the MEMS mirror array to modulate each of the wavelength components and wherein the controller is configured to detect the gases by digitizing and processing the electrical signals generated by the acoustic sensor.

18. The photoacoustic sensor of claim 17, wherein the unique modulation signals comprise maximum-length-sequence-based modulation signals.

19. The photoacoustic sensor of claim 15, wherein the input light beam is generated from one of a broadband visible light source, an IR light source, and a UV light source.

* * * * *

UNITED STATES PATENT AND TRADEMARK OFFICE
CERTIFICATE OF CORRECTION

Page 1 of 2

PATENT NO. : 8,561,454 B2
APPLICATION NO. : 13/202356
DATED : October 22, 2013
INVENTOR(S) : Muehleisen It is certified that error appears in the above-identified patent and that said Letters Patent is hereby corrected as shown below:

In the Drawings:

In Fig. 5, Sheet 5 of 5, below "PROCESSOR (504)" in Line 1, delete "UP/UC/" and insert -- µP/µC/ --, therefor.

In the Specifications:

In Column 3, Lines 54-55, delete "fast Hadamard transform (HFT)," and insert -- Fast Hadamard Transform (HFT), --, therefor.

In Column 4, Line 28, delete "A/D converter 14." and insert -- A/D converter 141. --, therefor.

In Column 5, Line 4, delete "MEMS-based optical switch 120" and insert -- MEMS-based optical modulator 120 --, therefor.

In Column 5, Lines 36-37, delete "MEMS-based optical switch 120" and insert -- MEMS-based optical modulator 120 --, therefor.

In Column 5, Line 48, delete "sounds waves" and insert -- sound waves --, therefor.

In Column 8, Lines 44-45,
delete "Fast Hadamard transforms (FHTs), fast Fourier transforms (FFTs)," and insert -- Fast Hadamard Transforms (FHTs), Fast Fourier Transforms (FFTs), --, therefor.

In Column 9, Lines 16-50, delete "PRBS used . . . . . . continuously." and insert the same at Line 15, after "particular" as a continuation paragraph.

Signed and Sealed this
Thirteenth Day of May, 2014

Michelle K. Lee
*Deputy Director of the United States Patent and Trademark Office*

CERTIFICATE OF CORRECTION (continued)
U.S. Pat. No. 8,561,454 B2

In Column 14, Line 62, delete "and or" and insert -- and/or --, therefor.

In the Claims:

In Column 16, Line 64, in Claim 1, delete "enemy" and insert -- energy --, therefor.

In Column 17, Line 39, in Claim 9, delete "sample:" and insert -- sample; --, therefor.

In Column 17, Line 61, in Claim 13, delete "mudulation" and insert -- modulation --, therefor.

In Column 17, Line 64, in Claim 13, delete "light wherein" and insert -- light, wherein --, therefor.